United States Patent
Cohen et al.

(10) Patent No.: US 12,128,040 B2
(45) Date of Patent: *Oct. 29, 2024

(54) SELECTIVE ESTROGEN RECEPTOR DEGRADERS

(71) Applicant: Eli Lilly and Company, Indianapolis, IN (US)

(72) Inventors: Jeffrey Daniel Cohen, Indianapolis, IN (US); Daniel Jon Sall, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 595 days.

This patent is subject to a terminal disclaimer.

(21) Appl. No.: 17/254,991

(22) PCT Filed: Jul. 11, 2019

(86) PCT No.: PCT/US2019/041342
§ 371 (c)(1),
(2) Date: Dec. 22, 2020

(87) PCT Pub. No.: WO2020/014440
PCT Pub. Date: Jan. 16, 2020

(65) Prior Publication Data
US 2021/0260052 A1 Aug. 26, 2021

Related U.S. Application Data

(60) Provisional application No. 62/825,172, filed on Mar. 28, 2019, provisional application No. 62/697,100, filed on Jul. 12, 2018.

(51) Int. Cl.
*A61K 31/4709* (2006.01)
*A61K 9/00* (2006.01)
*A61P 35/00* (2006.01)
*C07D 401/12* (2006.01)

(52) U.S. Cl.
CPC ........ *A61K 31/4709* (2013.01); *A61K 9/0053* (2013.01); *A61P 35/00* (2018.01); *C07D 401/12* (2013.01)

(58) Field of Classification Search
CPC .. A61K 31/4709; A61K 9/0053; A61K 45/06; A61P 35/00; C07D 401/12; C07D 491/052
USPC ........................................................ 514/210
See application file for complete search history.

(56) References Cited

U.S. PATENT DOCUMENTS

| | | | |
|---|---|---|---|
| 5,962,475 A | * 10/1999 | Schmid | C07D 333/56 546/202 |
| 10,654,866 B2 | * 5/2020 | Bastian | C07D 491/052 |
| 2007/0015817 A1 | 1/2007 | McKie et al. | |
| 2011/0281847 A1 | 11/2011 | Dally et al. | |
| 2017/0197915 A9 | 7/2017 | Liang et al. | |

FOREIGN PATENT DOCUMENTS

| WO | WO-9510513 A1 | * 4/1995 | ........... C07D 231/12 |
|---|---|---|---|
| WO | WO-2016097071 A1 | * 6/2016 | ........... A61K 31/381 |
| WO | WO-2018129387 A1 | * 7/2018 | ........... A61K 31/381 |

OTHER PUBLICATIONS

Zhichao Liu, Brian Delavan, Ruth Roberts, Weida Tong, Lessons Learned from Two Decades of Anticancer Drugs, Trends in Pharmacological Sciences, vol. 38, Issue 10, 2017, pp. 852-872 (Year: 2017).*
Kunnumakkara AB, Bordoloi D, Sailo BL, Roy NK, Thakur KK, Banik K, Shakibaei M, Gupta SC, Aggarwal BB. Cancer drug development: The missing links. Exp Biol Med (Maywood). May 2019;244(8): p. 663-689. (Year: 2019).*
Ur Rahman MS, Cao J. Estrogen receptors in gastric cancer: Advances and perspectives. World J Gastroenterol. Feb. 28, 2016;22(8):2475-82 (Year: 2016).*
Di Zazzo E, Galasso G, Giovannelli P, Di Donato M, Bilancio A, Perillo B, Sinisi AA, Migliaccio A, Castoria G. Estrogen Receptors in Epithelial-Mesenchymal Transition of Prostate Cancer. Cancers (Basel). Sep. 23, 2019;11(10):1418 (Year: 2019).*
Hsu LH, Chu NM, Kao SH. Estrogen, Estrogen Receptor and Lung Cancer. Int J Mol Sci. Aug. 5, 2017;18(8): 1713. (Year: 2017).*
Burwell, R.L., Chem. Rev. 1954, 54, 4, 615-685. (Year: 1954).*
Michael B. Smith, Chapter 6—Functional Group Exchange Reactions: Oxidations, Editor(s): Michael B. Smith, Organic Synthesis (Fourth Edition), Academic Press, 2017, pp. 215-307. (Year: 2017).*
Patel et al. Pharmacology & Therapeutics 186 (2018) 1-24, "Selective estrogen receptor modulators (SERMs) and selective estrogen receptor degraders (SERDs) in cancer treatment". (Year: 2018).*
McDonnell et al. J. Med. Chem. 2015, 58, 4883-4887, "Oral Selective Estrogen Receptor Downregulators (SERDs), a Breakthrough Endocrine Therapy for Breast Cancer". (Year: 2015).*
International Search Report of the International Searching Authority for PCT/US2019/041342 dated Jul. 11, 2019.
Written Opinion of the International Searching Authority for PCT/US2019/041342 dated Jul. 11, 2019.

* cited by examiner

*Primary Examiner* — Jared Barsky
*Assistant Examiner* — Liyuan Mou
(74) *Attorney, Agent, or Firm* — Bradley W. Crawford

(57) ABSTRACT

Novel selective estrogen receptor degraders (SERDs) according to the formula: pharmaceutically acceptable salts, pharmaceutical compositions, uses, and methods of use thereof are provided.

7 Claims, No Drawings

SELECTIVE ESTROGEN RECEPTOR DEGRADERS

BACKGROUND

Selective estrogen receptor degraders (SERDs) bind to the estrogen receptor (ER) and downregulate ER-mediated transcriptional activity. This degradation and downregulation caused by SERDs can be useful in the treatment of cell proliferation disorders, such as cancer. Some small molecule examples of SERDs have been disclosed in the literature (see, e.g., WO2005073204, WO2014205136, and WO2016097071). However, known SERDs have not yet been as useful as is needed to effectively treat cancer. For example, finding SERDs with better pharmacokinetic (PK) and pharmacodynamic (PD) properties, higher efficiency in the clinic, and good oral bioavailability would be very helpful in treating cancer. A pure antagonist SERD with potent inhibition of ER-mediated transcription would be expressly beneficial in treating cancer. There is a need for new SERDs to treat cancers such as breast cancer, ovarian cancer, endometrial cancer, prostate cancer, uterine cancer, gastric cancer, and lung cancer as well as mutations due to emerging resistance. In particular there is a need for new SERDs to treat ER positive breast cancer, gastric cancer, and/or the lung cancer

SUMMARY

A compound of the formula:

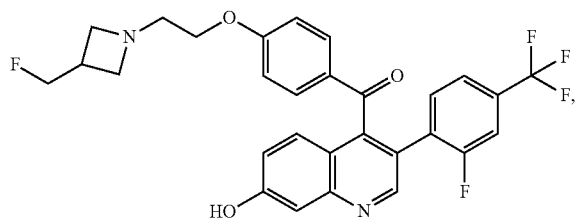 [SMILES: O=C(c1ccc(OCCN2CC(CF)C2)cc1)c1c(-c2ccc(C(F)(F)F)cc2F)cnc2cc(O)ccc12]

and pharmaceutically acceptable salts thereof, and pharmaceutical compositions thereof, are provided herein.

Methods of using a compound as described herein, pharmaceutically acceptable salts thereof, and pharmaceutical compositions thereof, to treat breast cancer, ovarian cancer, endometrial cancer, prostate cancer, uterine cancer, gastric cancer, or lung cancer are also provided. The methods include administering a therapeutically effective amount of a compound as described herein, or a pharmaceutically acceptable salt thereof, to a patient in need.

Further provided is the compound as described herein, and a pharmaceutically acceptable salt thereof, for use in therapy. The compound described herein, and pharmaceutically acceptable salts thereof, can be used in the treatment of breast cancer, ovarian cancer, endometrial cancer, prostate cancer, uterine cancer, gastric cancer, or lung cancer.

The use of a compound as described herein, and pharmaceutically acceptable salts thereof, for the manufacture of a medicament for treating breast cancer, ovarian cancer, endometrial cancer, prostate cancer, uterine cancer, gastric cancer, or lung cancer is further provided.

DESCRIPTION

A novel tetracyclic compound and pharmaceutical salts thereof that act as SERDs are disclosed herein. SERDs can be used either as single agents or in combination with other classes of drugs including selective estrogen receptor modulators (SERMs) aromatase inhibitors, CDK4 inhibitors, CDK6 inhibitors, PI3K inhibitors, and mTOR inhibitors to treat hormone receptor-positive breast cancer.

The novel compound described herein is a compound of the formula:

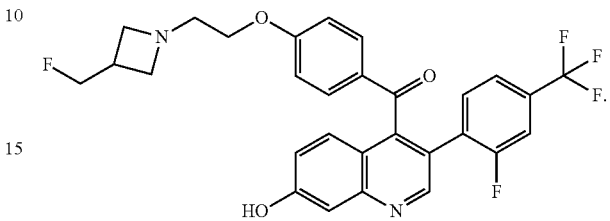

Pharmaceutically acceptable salts of the compound are also described. The compound can be named using IUPAC nomenclature as (4-{2-[3-(fluoromethyl)azetidin-1-yl]ethoxy}phenyl){3-[2-fluoro-4-(trifluoromethyl)phenyl]-7-hydroxyquinolin-4-yl}methanone.

Also described herein is a pharmaceutical composition including a compound as described herein, or a pharmaceutically acceptable salt thereof, in combination with a pharmaceutically acceptable excipient, carrier, or diluent. The pharmaceutical compositions described herein may be prepared using pharmaceutically acceptable additives. The term "pharmaceutically acceptable additive(s)" as used herein, refers to one or more carriers, diluents, and excipients that are compatible with the other additives of the compositions or formulations and not deleterious to the patient. The compound, or pharmaceutically acceptable salts thereof, described herein can be formulated as pharmaceutical compositions administered by a variety of routes, such as oral or IV. Bioavailability is often a factor in cancer treatment and the ability to tailor administration methods and pharmaceutical compositions to control or optimize the bioavailability of an active ingredient is useful. An orally bioavailable SERD composition would be particularly useful. The compound, or pharmaceutically acceptable salts thereof, as described herein are believed to have oral bioavailability. Examples of pharmaceutical compositions and processes for their preparation can be found in "Remington: The Science and Practice of Pharmacy", L. V. Allen Jr, Editor, 22$^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose and other cellulose derivatives, alginates, gelatin, and polyvinyl-pyrrolidone; kaolin and bentonite; polyethyl glycols.

Further described herein are methods of treating a cancer. The methods described herein include administering to a patient in need of such treatment an effective amount of a compound as described herein, or a pharmaceutically acceptable salt thereof. For example, the method of administering the effective amount of a compound as described herein, or pharmaceutically acceptable salt thereof, can be oral administration. The cancer can be an estrogen responsive cancer. Additionally, the cancer can be breast cancer, ovarian cancer, endometrial cancer, prostate cancer, uterine cancer, gastric cancer, or lung cancer. For example, the cancer can be ER positive breast cancer, ER positive gastric cancer, or ER positive lung cancer.

Also described herein is a compound as described herein, or a pharmaceutically acceptable salt thereof, for use in therapy. The compound as described herein, or pharmaceutically acceptable salts thereof, as described herein can be used in the treatment of breast cancer, ovarian cancer, endometrial cancer, prostate cancer, uterine cancer, gastric cancer, or lung cancer. In particular, the cancer can be ER positive breast cancer, ER positive gastric cancer, or ER positive lung cancer. For example, the compound, or pharmaceutically acceptable salt thereof, can be orally administered.

Additionally, for the compound as described herein, or pharmaceutically acceptable salts thereof, can be used in the manufacture of a medicament for the treatment of a cancer. For example, the medicament can be orally administered. The types of cancer the medicaments as described herein can be used to treat include breast cancer, ovarian cancer, endometrial cancer, prostate cancer, uterine cancer, gastric cancer, or lung cancer. In particular the cancer can be ER positive breast cancer, ER positive gastric cancer, or ER positive lung cancer.

The compound as described herein, and pharmaceutically acceptable salts thereof, may have clinical utility as a single agent or in combination with other anti-cancer agents, for the treatment of cancers such as breast cancer, ovarian cancer, endometrial cancer, prostate cancer, uterine cancer, gastric cancer, and lung cancer. When used in combination with other anti-cancer agents, the compound as described herein, or pharmaceutically acceptable salts thereof, can be used simultaneously, sequentially, or separately with the other anti-cancer agents. An example of an other anti-cancer agent that can be combined with the compound as described herein is 5-(4-{2-[3-(fluoromethyl)azetidin-1-yl]ethoxy}phenyl)-8-(trifluoromethyl)-5H-[1]benzopyrano[4,3-c]quinolin-2-ol.

As used herein, the term "effective amount" refers to the amount or dose of the compound as described herein, or pharmaceutically acceptable salts thereof, which, upon single or multiple dose administration to the patient, provides the desired effect in the patient under diagnosis or treatment. Preferably, a desired effect is inhibition of tumor cell proliferation, tumor cell death, or both. The compound as described herein, or pharmaceutically acceptable salts thereof, as described herein are generally effective over a wide dosage range. For example, dosages per day normally fall within the daily range of about 100 mg to about 2000 mg.

As used herein, "treat", "treating" or "treatment" refers to restraining, slowing, stopping, or reversing the progression or severity of an existing symptom or disorder.

As used herein, the term "patient" refers to a human which is afflicted with a particular disease, disorder, or condition.

The compound as described herein, or pharmaceutically acceptable salts thereof, as described herein may be prepared by a variety of procedures known in the art, some of which are illustrated in the Preparations and Example below. The specific synthetic steps for each of the routes described may be combined in different ways, or in conjunction with steps from different procedures, to prepare the compound as described herein, or pharmaceutically acceptable salts thereof. The products can be recovered by conventional methods well known in the art, including extraction, evaporation, precipitation, chromatography, filtration, trituration, and crystallization. The reagents and starting materials are readily available to one of ordinary skill in the art.

In an optional step, a pharmaceutically acceptable salt of a compound as described herein can be formed by reaction of an appropriate free base of the present invention with an appropriate pharmaceutically acceptable acid in a suitable solvent under standard conditions. Additionally, the formation of such salts can occur simultaneously upon deprotection of a nitrogen-protecting group. The possible formation of pharmaceutically acceptable salts is well known. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*. 66: 1-19, (1977). One of ordinary skill in the art will appreciate that a compound as described herein is readily converted to and may be isolated as a pharmaceutically acceptable salt.

Unless specifically noted, abbreviations used herein are defined according to *Aldrichimica Acta*, Vol. 17, No. 1, 1984, or the commonly accepted meaning of those of skill in the art. Other abbreviations are defined as follows: "AUC" refers to area under the curve; "BSA" refers to Bovine Serum Albumin; "DCM" refers to dichloromethane or methylene chloride; "DMA" refers to dimethylamine; "DMEM" refers to Dulbecco's Modified Eagle's Medium; "DMF" refers to N,N-dimethylformamide; "DMSO" refers to dimethyl sulfoxide; "DNA" refers to deoxyribonucleic acid; "cDNA" refers to complementary DNA; "DNase" refers to deoxyribonuclease; "DTT" refers to dithiothreitol; "$EC_{50}$" refers to the concentration of an agent which produces 50% response of the target activity compared to a predefined positive control compound (absolute $EC_{50}$); "EDTA" refers to ethylenediaminetetraacetic acid; "ERα" refers to estrogen receptor alpha; "EtOAc" refers to ethyl acetate; "EtOH" refers to ethanol; "FBS" refers to Fetal Bovine Serum; "HBSS" refers to Hank's Balanced Salt Solution; "HEPES" refers to 4-(2-hydroxyethyl)-1-piperazineethanesulfonic acid; "$IC_{50}$" refers to the concentration of an agent which produces 50% of the maximal inhibitory response possible for that agent, (relative $IC_{50}$), or the concentration of an agent which produces 50% inhibition of the target enzyme activity compared to placebo control (absolute $IC_{50}$); "iPrOH" refers to isopropanol or isopropyl alcohol; "IV" refers to intravenous administration; "$K_i$" refers to inhibition constant; "MeOH" refers to methyl alcohol or methanol; "MTBE" refers to methyl t-butyl ether; "PBS" refers to Phosphate Buffered Saline; "PO" refers to oral administration; "PRα" refers to progesterone receptor alpha; "QD" refers to once a day dosing; "RNA" refers to ribonucleic acid; "RNase" refers to ribonuclease; "RT-PCR" refers to reverse transcription polymerase chain reaction; "RT-qPCR" refers to reverse transcription quantitative polymerase chain reaction; "THF" refers to tetrahydrofuran; and "XPhos Pd G2" refers to chloro(2-dicyclohexylphosphino-2',4',6'-triisopropyl-1,1'-biphenyl)[2-(2'-amino-1,1'-biphenyl)]palladium(II).

The following Preparations and Examples further illustrate the invention.

PREPARATIONS AND EXAMPLES

Preparation 1

2-[3-(Fluoromethyl)azetidin-1-yl]ethan-1-ol

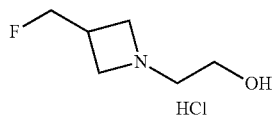

Add sodium triacetoxyborohydride (405 g, 1.91 mol) portion-wise over a period of 15 minutes to a stirred 0° C. solution of 3-(fluoromethyl)azetidine hydrochloride (160 g, 1.28 mol) in DCM (2.4 L) under $N_2$ and stir at 0° C. for 10 minutes. Add 1,4-dioxane-2,5-diol (99 g, 0.83 mol) at 0° C. in 6 portions over a period of 1 hour then stir at 0-5° C. for 15 minutes. Allow the reaction to warm to room temperature and stir for 2 hours under $N_2$. Cool the reaction to 10-15° C. over a period of 20 minutes. Add water (800 mL) over a period of 25-30 minutes at 10-15° C., allow to warm to room temperature for 5-10 minutes and then separate the layers. Wash the aqueous layer with DCM (800 mL), separate the layers then cool the combined aqueous layers to 10-15° C. and adjust the pH to 13-14 using 50% sodium hydroxide solution (~540 mL). Allow the aqueous layer to warm to room temperature, extract with DCM (4×800 mL), dry with sodium sulfate (80 g), filter, and concentrate to dryness to obtain the title compound. Following this preparation gave 139 g (82%) of the title compound as a thick yellow oil with an ES/MS (m/z) of 134.1 (M+H).

Preparation 2

2-[3-(Fluoromethyl)azetidin-1-yl]ethan-1-ol hydrochloride

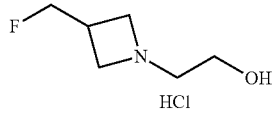

Dissolve 2-[3-(fluoromethyl)azetidin-1-yl]ethan-1-ol (529 g, 4 mol) in MTBE (2.6 L) and cool to 0° C. Add HCl/EtOH solution (492 mL, 30 wt %) drop-wise over 30 minutes then stir at 0° C. for 30 minutes. Filter the solids and wash the filter cake with MTBE (2×200 mL). Dry under $N_2$ for 8 hours to obtain the title compound. Following this preparation gave 580 g (86%) of the title compound as a white solid with an ES/MS (m/z) of 134.0 (M+H).

Preparation 3

(3-Chloro-7-methoxyquinolin-4-yl)-(4-fluorophenyl)methanone

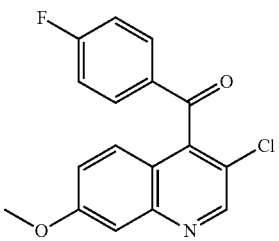 [SMILES: COc1ccc2c(C(=O)c3ccc(F)cc3)c(Cl)cnc2c1]

Cool a mixture of 4-bromo-3-chloro-7-methoxyquinoline (70 g, 254 mmol) and THF (1 L) to −40° C. under $N_2$ resulting in precipitation of the material. Add isopropylmagnesium chloride (2 M in THF, 254 mL, 509 mmol) over 20 minutes and stir the mixture for 1 hour. Add a solution of 4-fluorobenzoyl chloride (66 mL, 559 mmol) in THF (140 mL) drop-wise then allow to warm to room temperature. Quench the reaction with saturated ammonium chloride solution (300 mL) and water (200 mL) and separate the layers. Wash the organic layer with saturated ammonium chloride solution (300 mL), dry over $MgSO_4$, filter, and concentrate to provide an oily residue. Filter the crude brown oil through silica gel eluting with a mixture of MTBE/hexane (1:1) to obtain the crude product as a yellow solid (84 g). Treat the solid with 10% methylacetate/heptane (800 mL) and stir at room temperature overnight. Filter to collect the solids and reserve. Concentrate the filtrate and purify on silica eluting with 10-40% EtOAc/hexanes then treat the product with 10% methylacetate/heptane (200 mL) and stir at room temperature for 3 hours. Filter the resulting solids, combine with solids from the previous filtration and dry under vacuum overnight to obtain the title compound. Following this preparation gave 31 g (38%) of the title compound as a yellow solid with an ES/MS (m/z) of 316.0 (M+H).

Preparation 4

(3-Chloro-7-hydroxyquinolin-4-yl)-(4-fluorophenyl)methanone

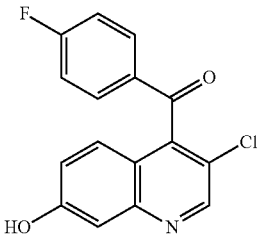 [SMILES: O=C(c1ccc(F)cc1)c1c(Cl)cnc2cc(O)ccc12]

Add boron tribromide (1 M in DCM, 295 mL, 295 mmol) to a mixture of (3-chloro-7-methoxyquinolin-4-yl)-(4-fluorophenyl)methanone (31 g, 98 mmol) in DCM (217 ml) and stir the mixture at room temperature for 3 days. Pour the mixture slowly into a 0° C. solution of dibasic potassium phosphate (2 M in water, 700 mL) and water (200 mL).

Allow the mixture to warm to room temperature and stir for 1 hour. Concentrate the solution in vacuo to remove organic solvents, filter, collect the filtrate and dry the filtrate under vacuum at 45° C. overnight. Treat the solids with DCM/heptane (1:1, 450 mL) and stir overnight. Collect the solids and dry under vacuum overnight to obtain the title compound. Following this preparation gave 32 g (quantitative yield) of the title compound as a light brown solid with an ES/MS (m/z) of 302.0 (M+H).

Preparation 5

(3-Chloro-7-hydroxyquinolin-4-yl)-(4-{2-[3-(fluoromethyl)azetidin-1-yl]ethoxy}phenyl)methanone

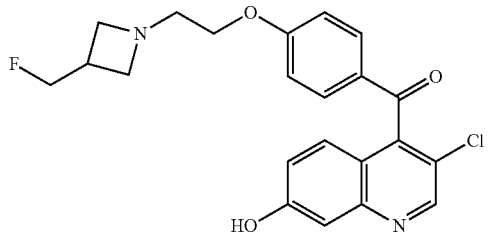 [SMILES: O=C(c1ccc(OCCN2CC(CF)C2)cc1)c1c(Cl)cnc2cc(O)ccc12]

Add 2-[3-(fluoromethyl)azetidin-1-yl]ethan-1-ol hydrochloride (3.90 g, 23.0 mmol) to a stirred solution of (3-chloro-7-hydroxyquinolin-4-yl)-(4-fluorophenyl)methanone (5.00 g, 15.3 mmol) in DMF (75 ml) followed by sodium hydride (60% in mineral oil, 3.07 g, 76.6 mmol). Stir under $N_2$ and warm to 40° C. for 45 minutes. Quench the solution with water and concentrate. Partition the residue between 20% iPrOH/CHCl$_3$ and saturated aqueous sodium bicarbonate solution and separate, extract the aqueous with 2×20% iPrOH/CHCl$_3$, combine the organic extracts, dry the combined organic layers over magnesium sulfate, filter and concentrate the filtrate to obtain the crude product as a dark red oil. Purify the crude material by silica gel column chromatography eluting with a gradient of 5-10% 7 N NH$_3$ in MeOH/DCM to give the title compound. Following this preparation gave 5.31 g (84%) of the title compound as a yellow solid with an ES/MS (m/z) of 415.0 (M+H).

Preparation 6

(4-Fluorophenyl)-[3-[2-fluoro-4-(trifluoromethyl)phenyl]-7-hydroxy-4-quinolyl]methanone

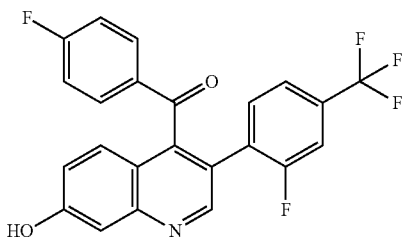 [SMILES: O=C(c1ccc(F)cc1)c1c(-c2ccc(C(F)(F)F)cc2F)cnc2cc(O)ccc12]

Degas/purge with 5×N$_2$ a mixture of (3-chloro-7-hydroxy-4-quinolyl)-(4-fluorophenyl)methanone (140 g, 440.8 mmol), 2-fluoro-4-(trifluoromethyl)phenylboronic acid (183.3 g, 881.7 mmol), potassium carbonate (184.6 g, 1.3 mol), 2-methyl-2-butanol (1.7 L) and water (0.56 L). Add XPhos Pd G2 (7.1 g, 8.82 mmol) and heat at 80° C. for 2 hours. Cool the mixture to room temperature and evaporate the organic solvent. Add EtOAc (1 L) and water (0.2 L). Separate the organic layer and dry it over magnesium sulfate. Filter this material through silica gel and concentrate to dryness. Triturate the crude material with a mixture of hexanes (1.25 L) and MTBE (0.25 L) to provide a solid. Filter the solid and dry under vacuum. Dissolve the solid in THF (1.5 L) and add a scavenger of SiliaMetS® Thiol (150 g). Stir the mixture at room temperature overnight. Filter the scavenger and evaporate the filtrate to dryness to give the title compound. Following this preparation gave 185.5 g (96%) of the title compound as a white solid with an ES/MS (m/z) of 430.0 (M+H).

Example 1

(4-{2-[3-(Fluoromethyl)azetidin-1-yl]ethoxy}phenyl){3-[2-fluoro-4-(trifluoromethyl)phenyl]-7-hydroxyquinolin-4-yl}methanone

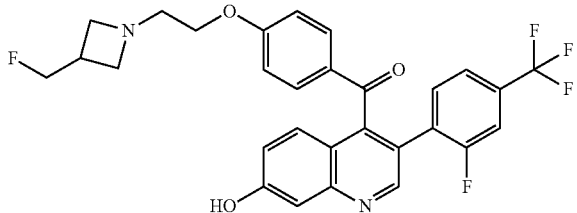 [SMILES: O=C(c1ccc(OCCN2CC(CF)C2)cc1)c1c(-c2ccc(C(F)(F)F)cc2F)cnc2cc(O)ccc12]

To a vessel, equipped with a N$_2$ inlet, add THF (2.8 L), potassium tert-butoxide (274.5 g, 2.45 mol) and 2-(3-(fluoromethyl)azetidin-1-yl)ethan-1-ol (168 g, 1.22 mol). Stir the mixture for 10 minutes. Add dropwise a solution of (4-fluorophenyl)-[3-[2-fluoro-4-(trifluoromethyl)phenyl]-7-hydroxy-4-quinolyl]methanone (350 g, 0.81 mol) in THF (0.7 L). Stir at room temperature for one hour. Quench the reaction with 1 N HCl until pH 8 and dilute with EtOAc (4 L). Separate the organic layer and wash it with brine (2 L). Dry the solution over magnesium sulfate, filter the solution, and concentrate to dryness to give the title compound. Following this preparation gave 415 g (93.8%) of the title compound as a pale brown solid with an ES/MS (m/z) of 543.2 (M+H).

Alternate Example 1

Degas/purge with N$_2$×5 a mixture (3-chloro-7-hydroxyquinolin-4-yl)-(4-{2-[3-(fluoromethyl)azetidin-1-yl]ethoxy}phenyl)methanone (200 mg, 0.48 mmol), 2-fluoro-4-(trifluoromethyl)phenylboronic acid (158 mg, 0.72 mmol), potassium carbonate (202 mg, 1.45 mmol), 2-methyl-2-butanol (3 ml), and water (1 ml) in a microwave vial. Add XPhos Pd G2 (12 mg, 0.015 mmol), seal the mixture, and microwave at 80° C. for 2 hours. Partition the residue between MTBE and saturated ammonium chloride solution. Separate the layers and extract the aqueous with MTBE. Combine the organic extracts, dry them over magnesium sulfate, filter, and concentrate the filtrate to obtain an orange residue. Purify the crude material by silica gel column chromatography eluting with of 5% MeOH/DCM to give the title compound. Following this preparation gave 205 mg (78%) of the title compound as a yellow solid with ES/MS (m/z) of 543.2 (M+H).

Example 2

Racemic 5-(4-{2-[3-(Fluoromethyl)azetidin-1-yl]ethoxy}phenyl)-8-(trifluoromethyl)-5H-[1]benzopyrano[4,3-c]quinolin-2-ol

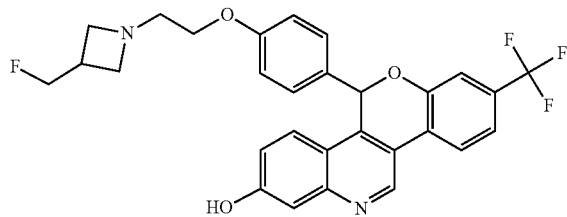 [SMILES: Oc1ccc2c3c(cnc2c1)-c1ccc(C(F)(F)F)cc1OC3c1ccc(OCCN2CC(CF)C2)cc1]

Cool a solution of (4-{2-[3-(fluoromethyl)azetidin-1-yl]ethoxy}phenyl){3-[2-fluoro-4-(trifluoromethyl)phenyl]-7-hydroxyquinolin-4-yl}methanone (5.27 g, 9.71 mmol) in 1,4-dioxane (100 mL) to 5° C. Add lithium triethylborohydride (1 M in THF, 30.0 mL, 30.0 mmol). Remove the cooling bath and stir for 1.5 hours at room temperature. Quench the mixture with water. Add saturated NH$_4$Cl solution and EtOAc. Separate the layers and extract the aqueous layer with EtOAc. Combine the organic extracts, dry over anhydrous MgSO$_4$, filter, and concentrate the filtrate. Dissolve the crude residue in THF (100 mL).

Add sodium hydride (60% in mineral oil, 1.94 g, 48.5 mmol). Heat Reflux the solution for 1.5 hours. Add additional sodium hydride (60% in mineral oil, 1.94 g, 48.5 mmol), then reflux for an additional 30 minutes. Cool the solution to room temperature and quench with water. Add EtOAc and saturated NH$_4$Cl solution. Separate the layers and extract the aqueous layer with EtOAc. Combine the organic extract, dry over anhydrous MgSO$_4$, filter, and concentrate the filtrate. Purify the residue by silica gel column chromatography eluting with a gradient of 5-7% MeOH in DCM to give the title compound (3.70 g, 72%) as a light yellow foam. ES/MS (m/z): 525.2 (M+H).

Biological Assays

The relationship between estrogen receptor expression and certain cancers has been reported in the literature, (for breast cancer see, e.g., Puhalla S, Bhattacharya S, Davidson N., Hormonal therapy in breast cancer: A model disease for the personalization of cancer care, Molecular Oncology, 2012, 6:222-236; Kennecke H, Yerushalmi R, Woods R, Cheang M C U, Voduc D, Speers C H, Nielsen T O, Gelmon K, Metastatic behavior of breast cancer subtypes, J Clin Oncol, 2010, 28(20):3271-3277; for ovarian cancer see, e.g., O'Donnell A J, Macleod K G, Burns D J, Smyth J F, Langdon S P, Estrogen receptor-alpha mediates gene expression changes and growth response in ovarian cancer cells exposed to estrogen, Endocr Relat Cancer, 2005; 12(4):851-66; Walker G, MacLeod K, Williams A R, Cameron D A, Smyth J F, Langdon S P, Estrogen regulated gene expression predicts response to endocrine therapy in patients with ovarian cancer, Gynecol Oncol, 2007, 106(3):461-8; Smyth J F, Gourley C, Walker G, MacKean M J, Stevenson A, Williams A R, et al., Antiestrogen therapy is active in selected ovarian cancer cases: The use of letrozole in estrogen receptor-positive patients, Clin Cancer Res, 2007, 13(12):3617-22; for prostate cancer see, e.g., Bonkohoff H, Fixemer T, Hunsicker I and Remberger K, Estrogen receptor expression in prostate cancer and premalignant prostate lesions, Am J Pathol, 1999, 155:641-647; for endometrial and uterine cancer see, e.g., Krasner C, Aromatase inhibitors in gynecologic cancer, J Steroid Biochem Mol Biol, 2007, August-September; 106(1-5):76-80; Boisen M M, Andersen C L, Sreekumar S, et al., Treating gynecologic malignancies with selective estrogen receptor downregulators (SERDs): Promise and challenges, Mol Cell Endocrinol, 2015, 418: 322-3330; For lung cancer see, e.g., Baik C S, Eaton K D et al., Estrogen signaling in lung cancer: An opportunity for novel therapy, Cancer, 2012, 4:969-988; Marquez-Garban D C, Chen H-W, Goodglick L, Fishbein M C and Pietras R J, Targeting aromatase and estrogen signaling in human non-small cell lung cancer. Steroid enzymes and cancer, Ann. N.Y. Acad Sci, 2009, 1155:194-205; Hamilton D H, Griner L M, Keller J M, Hu X, Southall N, Marugan J, David J M, Ferrer M and Palena C, Targeting estrogen receptor signaling with fulvestrant enhances immune and chemotherapy mediated cytotoxicity of human lung cancer, Clin Cancer Res, 2016, 22(24):6204-16; Rodriguez-Lara V, Hernandez-Martinez J M, Arrieta O, Influence of estrogen in non-small cell lung cancer and its clinical implications, J Thoracic Disease, 2018, 10(1):482-497; for gastric cancer see, e.g., Tang W, Liu R, Yan Y, Pan X, Wang M, Han X, Ren H, and Zhang Z, Expression of estrogen receptors and androgen receptor and their clinical significance in gastric cancer, Oncotarget, 2017, 8(25) 40765-777).

The following assays demonstrate that the exemplified compounds are potent degraders of ERα wild type and mutant proteins. The results of the assays also demonstrate that the exemplified compounds are potent antagonists of ERα wild type and mutant receptors and inhibit ER-mediated transcriptional activity. Additionally, the assays demonstrate that the compound of example 1 inhibits proliferation of ER+ breast cancer cell lines, and ERα signalling and tumor growth inhibition in a ER-positive breast cancer xenograft model.

ERα (Wild Type) and ERα (Y537S Mutant) Competition Binding Assay

The purpose of the following ER competition binding assays is to determine the binding affinity of a test compound against ERα (wild type) and ERα (Y537S mutant) See Fanning et al., "Estrogen receptor alpha somatic mutations Y537S and D538G confer breast cancer endocrine resistance by stabilizing the activating function-2 binding conformation," eLife 2016; 5:e12792.

Run the competition binding assay in a buffer containing 50 mM HEPES, pH 7.5, 1.5 mM EDTA, 150 mM NaCl, 10% glycerol, 1 mg/mL ovalbumin, and 5 mM DTT, using 0.025 Ci per well $^3$H-estradiol (118 Ci/mmol, 1 mCi/mL), 7.2 ng/well ERα (wild type), or 7.2 ng/well ERα (Y537S mutant). Add the test compound at 10 different concentrations ranging from 10,000 nM to 0.5 nM, and determine nonspecific binding in the presence of 1 μM of 17-3 estradiol. Incubate the binding reaction (140 μL) for 4 hours at room temperature, and then add cold dextran-charcoal buffer (70 μL) (containing per 50 mL of assay buffer, 0.75 g of charcoal and 0.25 g of dextran) to each reaction. Mix the plates for 8 minutes on an orbital shaker at 4° C. and then centrifuge at 3000 rpm at 4° C. for 10 minutes. Transfer an aliquot (120 μL) of the mixture to another 96-well, white flat bottom plate (Costar) and add Perkin Elmer Optiphase Supermix scintillation fluid (175 µL) to each well. Seal the plates and shake vigorously on an orbital shaker. After an incubation of 2.5 hours, read the plates in a Wallac Microbeta counter. Calculate the $IC_{50}$ using a 4-parameter logistic curve fit and calculate % inhibition at 10 µM. Convert the $IC_{50}$ values for the compound to $K_i$ using Cheng-Prusoff equation. The results of this assay demonstrate that the compound of Example 1 binds to recombinant ERα wild type with a $K_i$ (nM) of 3.78±0.74 (n=3) and binds to ERα mutant (Y537S) with a $K_i$ (nM) of 21.24±2.12 (n=3).

The results of this assay demonstrate the binding affinity and potency of exemplified compound against ERα wild type and mutant (ESR1 Y537S) proteins.

ERα Degradation Assay in MCF7 Cells

The purpose of the following ERα degradation assay is to measure the degradation of ERα by a test compound in an ERα positive breast cancer cell line such as MCF7.

Culture MCF7 (purchased from ATCC HTB-22) cells in DMEM media supplemented with 10% FBS, 0.01 mg/mL human insulin 1 and 1% penicillin/streptomycin antibiotics and plate in 384-well flat-bottom plates at a density of 4,000 cells per well in phenol red free DMEM media (20 µL) containing 10% charcoal stripped FBS. Incubate the cells overnight in a cell culture incubator (5% $CO_2$, 95% relative humidity and 37° C.) and allow the cells to attach to the plate. The following day dose the cells with the test compound. Use an Echo 555 acoustic dispenser to prepare test compound serial dilutions (1:3) in a range from 6 µM to 0.0003 µM. Dose the cells with the addition of 5 µL from the serial dilution plate to the cell plate producing a final DMSO concentration of 0.2% with a final test compound concentration dose range between 2 and 0.0001 µM. For the maximum point, use media containing 0.2% of DMSO and for the minimum point, use fulvestrant diluted at 2 µM final concentrations in the growth media containing 0.2% DMSO. After dosing with the test compound, incubate the cell plates at 37° C. and 5% $CO_2$ for 24 hours. Fix the cells by adding 14% para-formaldehyde (10 µL) for 30 minutes at room temperature. Wash the cells once with PBS (20 µL) and incubate with PBS (20 µL) containing 0.5% (v/v) TWEEN® 20 for 1 hour. Wash the cells with PBS containing 0.05% TWEEN® 20 (2×) and block with 3% BSA in PBS containing 0.05% TWEEN® 20 and 0.1% TRITON™ X-100 (20 µL/well) for 1 hour at room temperature. Add 1:500 Primary antibody (20 µL) (ERα (Clone SP1) monoclonal rabbit antibody #RM-9101-S, Thermo Scientific) dilution in 1% BSA in PBS containing 0.05% TWEEN® 20 per well, seal the plates and incubate overnight at 4° C. The following day wash the cells with PBS containing 0.05% TWEEN® 20 (2×) and incubate with secondary antibody (20 µL/well) (1:1000 dilution, Goat anti-rabbit IgM ALEXA FLUOR™ 488) in PBS 1% BSA for 105 minutes at room temperature. After washing plates with PBS (2×20 µL), add RNase (Sigma) (20 µL of 50 µg/mL) and 1:1000 propidium iodide dilution in PBS per well (20 µL). Seal the plates and incubate 1 hour at room temperature on the bench (preserved from light). Scan the plates with ACUMEN EXPLORER™ [Laser-scanning fluorescence microplate cytometer manufactured by TTP LABTECH LTD] to measure ERα. Image analysis is based on cellular fluorescent signals for identifying positive cells. Identify estrogen receptor positive cells by mean intensity. Use total intensity at 575-640 nm from propidium iodide/DNA to identify individual cells. Assay output is % estrogen receptor positive cells. Determine the $IC_{50}$ by curve fitting to a four parameter logistic for each output using GENE DATA™.

The results of this assay demonstrate that the compound of formula (I) is a SERD with potent ERα degradation activity in cells. Specifically, the results show potent degradation of ERα by the compound of Example 1 in MCF7 breast cancer cells. Using this assay, the Relative $IC_{50}$ (µM) value for the compound of Example 1 is 2.16±0.96 nM (n=15).

PRα Induction Assay in MCF7 Cells

The purpose of the following PRα induction assay is to determine whether a test compound has agonistic activity against ERα receptor (an agonist would be expected to activate the receptor.)

Culture MCF7 (purchased from ATCC HTB-22) in DMEM media supplemented with 10% FBS, 0.01 mg/mL human insulin 1 and 1% penicillin/streptomycin antibiotics and plate the cells (prior to becoming 70% confluent) in 384-well flat-bottom plates at a density of 4,000 cells per well in 20 µL volume in DMEM phenol red free media containing 10% FBS (charcoal stripped). Incubate the cells overnight in a cell culture incubator (5% $CO_2$, 95% relative humidity at 37° C.) and allow the cells to attach to the plate. The following day, dose the cells with test compound. Use an Echo 555 acoustic dispenser to prepare compound serial dilutions (1:3) in a range from 6 µM to 0.0003 µM. Dose the cells with the addition of the test compound (5 µL) from the serial dilution plate to the cell plate producing a final DMSO concentration of 0.2% with a final concentration of the test compound dose range between 2 and 0.0001 µM. For the maximum point use media containing 0.2% of DMSO and for the minimum point, use fulvestrant diluted at 2 µM final concentrations in the growth media containing 0.2% DMSO. After dosing with the test compound, incubate the cell plates at 37° C. and 5% $CO_2$ for 24 hours. Fix the cells by adding 14% para-formaldehyde (10 µL) for 30 minutes at room temperature. Wash cells once with PBS (20 µL) and incubate with PBS (20 µL) containing 0.5% (v/v) TWEEN® 20 for 1 hour. Wash cells twice with PBS (20 µL) containing 0.05% TWEEN® 20 and block with 3% BSA in PBS containing 0.05% TWEEN® 20 and 0.1% TRITON™ X-100 (20 µL/well) for 1 hour at room temperature. Add 1:500 primary antibody (20 µL) (Progesterone receptor monoclonal mouse anti-human antibody, clone PgR 636 Dako, M3569) dilution in 1% BSA/PBS with 0.05 TWEEN® 20 per well, seal the plates and incubate overnight at 4° C.

The following day, wash cells with PBS 0.05% TWEEN® 20 (2×20 µL) and incubate with secondary antibody (20 µL/well) (1:1000 dilution, Goat anti-rabbit IgM ALEXA FLUOR™ 488) in PBS 1% BSA for 105 minutes at room temperature. After washing with PBS (2×20 µL), add RNase (20 µL of 50 µg/mL) (Sigma) and 1:1000 propidium iodide dilution in PBS per well. Seal plates and incubate 1 hour at room temperature on the bench (preserved from light). Scan plates with ACUMEN EXPLORER™ [Laser-scanning fluorescence microplate cytometer manufactured by TTP LABTECH LTD] to measure progesterone receptor alpha. Image analysis is based on cellular fluorescent signals for identifying positive cells. Identify progesterone receptor positive cells by mean intensity. Use total intensity at 575-640 nm from propidium iodide/DNA to identify individual cells. Assay output is % progesterone receptor positive cells. Determine the $IC_{50}$ by curve fitting to a four parameter logistic for each output using GENE DATA™.

Using this assay, the Relative IC$_{50}$ (µM) of the compound of Example 1 is >2 µM. The results of this assay demonstrate no significant agonistic activity of Example 1 in MCF7 breast cancer cells. These results also demonstrate that the compound of Example 1 is a pure antagonist of ERα in MCF7 breast cancer cells.

PRα Inhibition (ERα Functional Antagonism) Cell Assay in MCF7-ESR1 Y537N 682 CRISPR Cells The purpose of the following PRα inhibition (ERα functional antagonism) cell assay is to determine the antagonistic activity of a test compound against the Y537N mutant ERα receptor. An antagonist in this assay is expected to block the function of the ERα receptor. PRα (PGR) is a downstream transcriptional target of ERα and hence an antagonist of ERα is expected to inhibit the expression of PRα.

Culture MCF7-ESR1 Y537N-682 (generated by CRISPR/Cas9 gene editing of ESR1 gene in MCF7 cells, clone #682) in DMEM media supplemented with 10% FBS and 1% penicillin/streptomycin antibiotics and plate the cells (prior to becoming 70% confluent) in 384-well flat-bottom plates at a density of 4,000 cells per well in DMEM phenol red free media 10% FBS (20 µL volume) (charcoal stripped). Incubate the cells overnight in a cell culture incubator (5% $CO_2$, 95% relative humidity and 37° C.) and allow the cells to attach to the plate. The following day dose the cells with the test compound. Use an Echo 555 acoustic dispenser to prepare compound serial dilutions (1:3) in a range from 6 µM to 0.0003 µM. Dose the cells with the addition of 5 µL from the serial dilution plate to the cell plate producing a final DMSO concentration of 0.2% with a final test compound concentration dose range between 2 and 0.0001 µM. For the maximum point use media containing 0.2% of DMSO and for the minimum point, use fulvestrant diluted at 2 µM final concentrations in the growth media containing 0.2% DMSO. After dosing with test compound, incubate the cell plates at 37° C. and 5% $CO_2$ for 72 hours. Fix the cells by adding 14% para-formaldehyde (10 µL) for 30 minutes at room temperature. Wash the cells with PBS (1×20 µL) and incubate with PBS (20 µL) of containing 0.5% (v/v) TWEEN® 20 for 1 hour. Wash the cells with PBS (2×20 µL), 0.05% TWEEN® 20, and block with 3% BSA/PBS 0.05% TWEEN® 20, 0.1% TRITON™ X-100 (20 µL/well) for 1 hour at room temperature. Add 1:500 primary antibody (20 µL) (Progesterone receptor monoclonal mouse anti-human antibody, clone PgR 636 Dako, M3569) dilution in 1% BSA/PBS 0.05 TWEEN® 20 per well, seal the plates and incubate overnight at 4° C.

The following day, wash the cells with PBS 0.05%® (2×20 µL) and incubate with secondary antibody (20 µL/well) (1:1000 dilution, Goat anti-rabbit IgM ALEXA FLUOR™ 488) in PBS 1% BSA for 105 minutes at room temperature. After washing with PBS (2×20 µL), add RNase (20 µL of 50 µg/mL) (Sigma) and 1:1000 propidium iodide dilution in PBS per well. Seal the plates and incubate 1 hour at room temperature on the bench (preserved from light). Scan the plates with ACUMEN EXPLORER™ [Laser-scanning fluorescence microplate cytometer manufactured by TTP LABTECH LTD] to measure progesterone receptor alpha. Image analysis is based on cellular fluorescent signals for identifying positive cells. Identify progesterone receptor positive cells by mean intensity. Use total intensity at 575-640 nm from propidium iodide/DNA to identify individual cells. Assay output is % progesterone receptor positive cells. Determine the IC$_{50}$ by curve fitting to a four parameter logistic for each output using GENE DATA™.

Using this assay, the Relative IC$_{50}$ (nM) of the compound of Example 1 is 7.602±4.804 nM (n=14). These results demonstrate potent inhibition of PRα and functional antagonism by Example 1 in MCF7 (ESR1 Y537N, heterozygous mutant) breast cancer cells. As such, the compound of Example 1 is a potent antagonist of ERα mutant (Y537N) and a potent inhibitor of ERα mediated transcription. PRα (PGR) is also a transcriptional target of ERα and the results from this assay demonstrate potent inhibition of ERα-mediated transcription of PRα.

PRα Inhibition (ERα Functional Antagonism) Cell Assay in MCF7 Cells

The purpose of the following PRα inhibition (ERα functional antagonism) cell assay is to determine the antagonistic activity of a test compound against the ERα receptor. An antagonist in this assay is expected to block the function of the ERα receptor. PRα is a downstream transcriptional target of ERα and hence an antagonist of ERα is expected to inhibit the expression of PRα.

Carry out the assay conditions as detailed in the ERα degradation Cell base Acumen assay above, using the MCF7 cell line except that, prior to test compound dispensing, remove the media from the cell plate and pretreat all wells except for the negative control wells (column 24 of the plate) with assay media containing 0.47 nM estradiol for 30 minutes. In this assay, carry out immunostaining for the detection of PRα and scan the plates with ACUMEN EXPLORER™ [Laser-scanning fluorescence microplate cytometer manufactured by TTP LABTECH LTD] to measure PRα. Image analysis is based on cellular fluorescent signals for identifying positive cells. Identify PRα positive cells by mean intensity. Use total intensity at 575-640 from propidium iodide/DNA to identify individual cells. Assay output is % PRα positive cells. Determine the IC$_{50}$ by curve fitting to a four parameter logistic for each output using GENE DATA™.

Using this assay, the Relative IC$_{50}$ (nM) of the compound of Example 1 in this assay is 15.75±9.037 nM (n=15). The results of this assay demonstrate potent inhibition of PRα and functional antagonism by Example 1 in MCF7 breast cancer cells. As such, the compound of Example 1 is a potent antagonist of ERα wild-type protein and a potent inhibitor of ERα mediated transcription. PRα (PGR) is also a transcriptional target of ERα and the results from this assay demonstrate potent inhibition of ERα-mediated transcription of PRα.

Cell Proliferation Assay in MCF7 and MCF7-ESR1 Y537N-682

The purpose of the following cell proliferation assays generally is to detect whether a test compound has effects on cell proliferation, cell viability, and cytotoxicity in response to treatment in cell culture experiments. Cell proliferation is monitored by monitoring the number of cells over time and the propodeum iodide assay used allows continuous measurement of cell viability over time.

Seed MCF7 (purchased from ATCC HTB-22) cells at a density of 2,000 cells per well in DMEM phenol red free media 10% FBS (20 µL volume) (charcoal stripped) into a clear bottom 384-well cell culture plate. Plate MCF7-ESRY537N-682 (generated by CRISPR/Cas9 gene editing of ESR1 gene in MCF7 cells, clone #682) in DMEM media supplemented with 10% FBS, and 1% penicillin/streptomycin antibiotics at a density of 1000 cells per well. Incubate the plates at 37° C. and 5% $CO_2$. The following day dose the cells with the test compound. Use an Echo 555 acoustic dispenser to prepare test compound serial dilutions (1:3) in a range from 60 μM to 0.003 μM. Dose the cells with the addition of 5 μL from the serial dilution plate to the cell plate, producing a final DMSO concentration of 0.2% with a final test compound concentration dose range between 20 and 0.001 μM. For the maximum point use media containing 0.2% of DMSO and for the minimum point use fulvestrant diluted at 2 μM final concentrations in the growth media containing 0.2% DMSO. After dosing with the test compound, incubate the cell plates at 37° C. and 5% $CO_2$. Seven days after test compound addition, remove the plates from the incubator and add cold ethanol 96% (65 μL) to each well. After 30 minutes, remove the media and add RNase (20 μL of 50 g/mL) (Sigma) and 1:1000 propidium iodide dilution in PBS per well. Seal the plates and incubate 1 hour at room temperature on the bench (preserved from light). Scan the plates with ACUMEN EXPLORER™ [Laser-scanning fluorescence microplate cytometer manufactured by TTP LABTECH LTD]. The MCF-7 cell line grows forming aggregates, cell number as number of objects may not be able to be used as readout; so the cell number may be evaluated through estimated number of cells (calculated through the area parameter (ratio of total area of the total cells population (a designated range of peak intensity of FL-1 (PI) and the mean area of the single cells population (defined by perimeter)). Determine the $IC_{50}$ by curve fitting to a four parameter logistic for each output using GENE DATA™.

Using this assay, the Relative $IC_{50}$ (nM) of the compound of Example 1 in MCF7 ESR1 wild type is 9.243±1.741 nM (n=2) and in MCF7-ESR1 Y537N mutant cells is 7.960±3.691 nM (n=6). These results demonstrate potent anti-proliferative activity and cell growth inhibition by Example 1 in MCF7 (ESR1 wild type) and MCF7 (ESR1 Y537N mutant) breast cancer cells.

In Vivo Target Inhibition (IVTI) Assay (PGR RT-qPCR Assay) in MCF7 Tumors

The purpose of this IVTI assay is to measure the ability of a test compound (SERD) to inhibit PGR (Progesterone Receptor alpha) gene expression (transcription) downstream of ERα in xenograft tumors implanted in mice.

Implant female NOD SCID mice (22-25 g) from Envigo RMS, Inc., Madison, Wisconsin with 5×10e⁶ MCF7 ER+ve breast cancer cells (ATCC, #HTB-22) subcutaneously in the right flank region in 1:1 HBSS+MATRIGEL™ solution (200 μL). Implant a 17-Q estradiol pellet (0.18 mg/pellet, 90 day release, from Innovative research) subcutaneously 1 day prior to tumor cell implantation. Measure tumor growth and body weight twice per week beginning the seventh day after the implantation. When tumor sizes reach 250-350 mm³, randomize animals and group into groups of five animals. Dose animals with either the test compound in a specific vehicle (1% hydroxyethylcellulose/0.25% TWEEN® 80/0.05% Antifoam in purified water) or vehicle alone orally for 3 days and collect tumors and blood at desired time intervals after last dose. Sacrifice animals using isoflurane anesthesia plus cervical dislocation. Flash freeze tumors and store at −80° C. until processing for RNA isolation and RT-qPCR assay. Collect blood in EDTA tubes, spin down for plasma, and freeze at −80° C. in a 96-well plate. Determine test compound exposures using mass spectrometry.

Pulverize tumors in liquid nitrogen and lyse in 1×RNA lysis buffer (from RNA isolation kits) using Matrix D beads (MP Biomedical, #6913-500) in a FASTPREP-24™ Cell Disrupter machine (MP Biomedical). Transfer tumor lysates to fresh tubes after spinning at 14000 rpm for 20 minutes at 4° C. Isolate RNA from tumor lysates using PURELINK® RNA Mini Kit (Invitrogen #12183018A) or RNeasy Mini Kit (Qiagen #74104 and #74106). Remove DNA contaminants using PURELINK® DNase Set (Invitrogen #12185010) or RNase-Free DNase Set (Qiagen #79254). Measure isolated RNA concentration by diluting samples in RNase free water and measuring the absorbance at 260 nm on a plate reader (SpectraMax190). Subtract the average 260 nm absorbance measurement of the blank (RNase free water only) from the 260 nm measurements of all other RNA samples. Dilute RNA samples to equal concentrations in RNase free water. Synthesize cDNA from diluted RNA using First-Strand Synthesis System for RT-PCR (Invitrogen, #18080-051). To perform RT-qPCR, first dilute cDNA in RNase free water. Combine 2× Absolute Blue qPCR ROX Mix (Thermo, #AB-4139/A), PGR primer (Thermo, Hs01556702_m1), and diluted cDNA for each reaction in a PCR plate (Applied Biosystems, #4309849). Amplify cDNA by incubating the samples for 2 minutes at 50° C. followed by 15 minutes at 95° C. in the thermocycler (ABI Prism 7900HT Sequence Detection System). Continue to incubate at 95° C. for 15 seconds followed by 50° C. for 60 seconds for a total of 40 cycles. Cycles are normalized to the housekeeping gene and used to calculate % PGR inhibition compared to the vehicle alone. Analyze each sample in duplicate and use average numbers for calculations. Calculate the percent target (PGR) inhibition using Excel and XL Fit.

The results of this assay demonstrates that the compound of Example 1 inhibits PRα (PGR) expression in the tumor xenograft model. Additionally, the compound of Example 1 inhibits PRα (PGR) expression by 57% in the tumor xenograft model for 24 hours with 30 mg/kg dose when administered orally. These results demonstrate significant and sustained inhibition of ERα antagonistic activity and ERα-mediate transcriptional activity in vivo in a tumor xenograft model.

In Vivo Tumor Growth Inhibition Study in MCF7 Xenograft Tumor Implanted in Mice

The purpose of the following xenograft tumor growth inhibition assay is to measure reduction in tumor volume in response to test compound administration.

Expand human breast cancer cells MCF7 (ATCC #HTB-22) in culture, harvest and inject 5×10e⁶ cells in 1:1 HBSS+MATRIGEL™ solution (200 μL) subcutaneously on to the rear right flank of female NOD SCID mice (22-25 g, Envigo RMS, Inc). Twenty-four hours prior to implantation of MCF7 cells, implant estrogen pellets (0.18 mg/pellet, 170 estradiol, 90-day release, Innovative Research) subcutaneously. Measure tumor growth and body weight twice per week beginning the seventh day after the implantation. When tumor sizes reach 250-350 mm³, randomize animals and group into groups of 5 animals. Prepare the test compound in an appropriate vehicle (1% hydroxyethylcellulose/ 0.25% TWEEN® 80/0.05% Antifoam in purified water) and administer by oral gavage for 42 days. Determine tumor response by tumor volume measurement performed twice a week during the course of treatment. Take the body weight as a general measure of toxicity whenever tumor volume is measured.

When used in this assay, the compound of Example 1 is found to have delta T/C % values as provided in Table 6 below. These results indicate that the compound of Example 1 demonstrates good oral bioavailability in mice and significant anti-tumor activity or tumor regressions in an MCF7 human breast cancer xenograft model.

In Vivo Tumor Growth Inhibition Study in MCF7 Xenograft Tumor Implanted in Mice

TABLE 6

| Tumor Model | Dose (mg/kg) | Schedule | Delta T/C % or Regression % | p-value |
|---|---|---|---|---|
| MCF7 (Breast Cancer Xenograft) | 30 | QD | −36 | <0.001* |

Analysis for tumor volume is based on Log 10 and SpatialPower covariance structure.
*significant (p < 0.05) compared to vehicle control.
Delta T/C % is calculated when the endpoint tumor volume in a treated group is at or above baseline tumor volume. The formula is $100 * (T - T_0)/(C - C_0)$, where T and C are mean endpoint tumor volumes in the treated or control group, respectively. $T_0$ and $C_0$ are mean baseline tumor volumes in those groups.
Regression % is calculated when the endpoint volume is below baseline. The formula $100 * (T - T_0)/T_0$, where $T_0$ is the mean baseline tumor volume for the treated group.
Grand mean of all groups from baseline (randomization) at day 32 is used to compute % change of T/C.

Rat Oral Bioavailability Assay

The purpose of the following assay is to demonstrate whether a test compound is orally bioavailable.

Administer the test compound to Sprague-Dawley rats IV at 1 mg/kg (using vehicles of either: 20% CAPTISOL© in 25 mM sodium phosphate buffer, pH2 quantum satis; or 25% DMA, 15% EtOH, 10% propylene glycol, 25% 2-pyrrolidone, and 25% purified water) and PO at 10 mg/kg (using a vehicle of 1% hydroxyethyl cellulose, 0.25% polysorbate 80, 0.05% Antifoam 1510-US, and purified water quantum satis). Collect serial blood samples at 0.08, 0.25, 0.5, 1, 2, 4, 8, and 12 hours post dose for IV bolus and at 0.25, 0.5, 1, 2, 4, 8, and 12 hours post dose after oral administration. After treatment with an EDTA coagulant, obtain plasma by centrifugation and stored at −70° C. until analysis by LC-MS/MS. Determine the test compound concentration in plasma and upload into the Watson LIMS™ system where noncompartmental analysis is used to calculate Area Under the Curve (AUC) for both IV and PO arms. Calculate oral bioavailability (% F) via the following equation, $$\% F = (AUC_{PO} \times Dose_{IV})/(AUC_{IV} \times Dose_{PO}) \times 100.$$

Using this assay, the compound of Example 1 displays a % F value of 27%. This assay demonstrates that Example 1 has good oral bioavailability.

What is claimed:
1. A compound of the formula

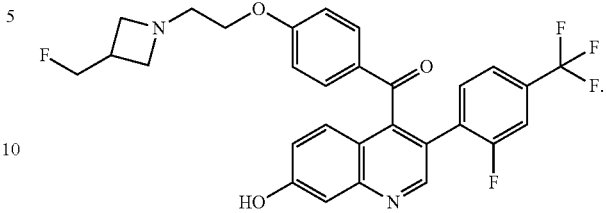

or a pharmaceutically acceptable salt thereof.

2. The compound according to claim 1, wherein the compound is

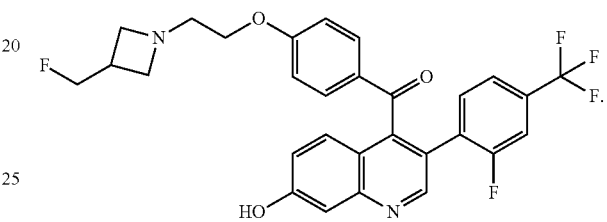

3. A pharmaceutical composition comprising the compound of claim 1, or a pharmaceutically acceptable salt thereof in combination with one or more pharmaceutically acceptable excipients, carriers, or diluents.

4. A method of treating breast cancer, ovarian cancer, endometrial cancer, or uterine cancer, comprising administering a therapeutically effective amount of a compound of claim 1, or a pharmaceutically acceptable salt thereof, to a patient in need of such treatment.

5. The method of claim 4, herein the compound, or a pharmaceutically acceptable salt thereof, is administered orally.

6. A method of treating ER positive breast cancer comprising administering a therapeutically effective amount of a compound of claim 1, or a pharmaceutically acceptable salt thereof, to a patient in need of such treatment.

7. The method according to claim 6, wherein the therapeutically effective amount of a compound of claim 1, or a pharmaceutically acceptable salt thereof is orally administered to a patient in need of such treatment.

* * * * *